United States Patent
Babson et al.

(10) Patent No.: US 6,849,457 B1
(45) Date of Patent: Feb. 1, 2005

(54) BEAD DISPENSER AND BEAD DISPENSER SYSTEM FOR IMMUNOASSAY ANALYSIS

(75) Inventors: Arthur L. Babson, Chester, NJ (US); Ilya Malyarov, Livingston, NJ (US)

(73) Assignee: DPC Cirrus, Inc., Randolph, NJ (US)

( * ) Notice: Subject to any disclaimer, the term of this patent is extended or adjusted under 35 U.S.C. 154(b) by 0 days.

(21) Appl. No.: 09/564,709

(22) Filed: May 4, 2000

(51) Int. Cl.⁷ .............................................. G65N 37/00
(52) U.S. Cl. ............................. 436/43; 422/63; 422/64; 422/103; 422/104; 436/807; 436/47; 221/264; 221/276
(58) Field of Search ........................... 436/48, 807, 47, 436/100, 43; 422/63, 64, 103, 104; 221/264, 276

(56) References Cited

U.S. PATENT DOCUMENTS

| | | |
|---|---|---|
| 1,602,358 A | 10/1926 | Getskay |
| 2,399,199 A | 4/1946 | Brandon |
| 2,683,554 A | 7/1954 | Mulhauser, Jr. |
| 3,946,913 A | 3/1976 | Merman |
| 4,101,284 A | 7/1978 | Difiglio et al. |
| 4,230,236 A | 10/1980 | Boulter |
| 4,354,619 A | 10/1982 | Wippermann et al. |
| 4,405,060 A | 9/1983 | Hsei |
| 4,415,098 A | 11/1983 | Haas |
| 4,492,316 A | 1/1985 | Emms |
| 4,937,048 A | 6/1990 | Sakai et al. |
| 5,316,726 A | 5/1994 | Babson et al. |
| 5,773,296 A | 6/1998 | Montalbano et al. |

Primary Examiner—Jill Warden
Assistant Examiner—Sam P. Siefke
(74) Attorney, Agent, or Firm—Whitham, Curtis & Christofferson, PC

(57) ABSTRACT

A bead dispenser device useful for supplying, one at a time, beads for heterogenous immunoassay, including an inner chamber having a return spring integrally formed to the inner chamber. The bead device also includes a plunger housed within a plunger chamber. The plunger includes a bead holding member and a notch. The return spring communicates with the notch of the plunger and biases the plunger in a resting position. In the resting position, the bead holding member is aligned with a bead receiving channel formed partly in the base of the inner chamber. When the plunger is depressed, the bead residing in the bead holding member is transported to a bead exit opening for dispensing therefrom. In this position, the return spring is also displaced inward to an inner portion of the inner chamber and is capable of agitating and contacting the beads located within the inner chamber. This ensures that the beads will not block or bridge the bead receiving channel which communicates with the bead holding chamber of the plunger.

24 Claims, 5 Drawing Sheets

BEAD DISPENSER AND BEAD DISPENSER SYSTEM FOR IMMUNOASSAY ANALYSIS

BACKGROUND OF THE INVENTION

1. Field of the Invention

The present invention generally relates to a bead dispenser and, more particularly, to a bead dispenser system adapted for dispensing beads in an automated immunoassay analyzer.

2. Background Description

An immunoassay is a well known laboratory method used to determine the amount of an analyte in a sample such as plasma or urine. It is based on the interaction of antibodies with antigens, and because of the degree of selectivity for the analyte (either antigen or antibody), an immunoassay can be used to quantitatively determine very low concentration of drugs, hormones, polypeptides, or other analyte compounds found in a test sample. For many years, immunoassays were performed by hand by trained laboratory technicians.

Recently, many companies have begun producing automated immunoassay analyzers. Automating the immunoassay procedures can be onerous because of the large number of steps needed to be executed. For example, in a conventional scheme, a sample is mixed with a reagent and a solid support having a bound antigen or antibody. The sample is incubated such that the corresponding antigen or antibody in the sample and a labeled antigen or antibody provided in the reagent can be bound to the antigen or antibody on the solid support. The solid support is then thoroughly washed and the label (fluorescent, radioactive, chemiluminescent, or the like) is detected by an appropriate mechanism. Finally, the analyte of interest (antigen or antibody) is quantified from the detected label.

Most of today's automated immunoassay analyzers are designed for "walk away" operation, where the technician loads sample containing tubes onto a carousel and presses a start button. Thereafter, the automated immunoassay analyzer mixes appropriate reagents (often stored aboard the analyzer) with the sample, performs incubating and washing operations, detects the label, and computes the quantity of analyte in the sample from the detected label and stored calibration curves. The entire operation is typically done under computer control, and is some automated immunoassay analyzers, bar coding is used to identify the sample under test. The results of the immunoassays are typically output onto computer paper for inspection by the technician, or monitored and displayed in real time as described in U.S. Pat. No. 5,316,726.

One conventional method for introducing a solid support bearing the appropriate antibody or antigen for the desired test on the analyte is by dropping a solid support in bead form into a test tube, and then the sample and reagents are added and the desired analysis conducted. For example, a trade brochure published by Olympus (Biomedical Products Division), Wendenstrasse 14-16, 2 Hamburg 1, Germany, describes a bead storage unit comprising a plurality of bead packs mounted on a carousel. Each bead pack stores a plurality of solid support beads as a column on a spiral track, where the beads exit the bottom of the spiral track into an open-air holding receptacle adjoining the outside of the base of the bead pack. The dispensed beads are picked up by a vacuum-operated bead transport for feeding into a U-shaped reaction tube.

Another conventional bead pack is marketed by Roche Laboratories. The Roche Laboratories bead pack includes a spiral track for storing solid support beads with support beads dispensed at a centrally-located exit hole. A three-pronged mechanical pick-up device is used to grasp and transport the dispensed bead to a reaction tube.

Abbott Laboratories also manufacturers a bead dispenser device. In this device, a manual operated dispenser with a plunger housed in a chamber in a non-hermetic manner is provided. The chamber has a lower exit opening that is horizontally misaligned relative to an upper feed hole into the chamber. The plunger has a receptacle hole for receiving a bead that is aligned with the upper feed hole in the normal non-actuated position of the plunger. Manual actuation of the plunger displaces the plunger horizontally within the chamber such that a bead carried in the plunger receptacle hole is carried to and over the lower exit opening in the chamber. At this stage the bead can drop out of the dispenser device.

Still other bead dispensing devices are disclosed in several U.S. Patents. However, the bead dispensing devices disclosed in the several patents all have the shortcoming that beads may block or bridge the bead discharging opening, and that there does not appear to be any mechanism for clearing the pathway in front of the bead discharging opening.

For example, U.S. Pat. No. 2,683,554 to Mulhauser discloses a pill dispenser having a threaded neck and a central funnel portion by which tablets can be directed to an opening. At the bottom of the opening is a slide having a stop portion which prevents the pills from being discharged from the pill dispenser. The slide is spring biased in the closed position. When the slide is depressed, the stop is moved and the tablet is discharged from the opening. In Mulhauser, however, the funnel may become blocked or bridged by several tablets.

By way of further example, U.S. Pat. No. 4,101,284 to Difiglio et al. shows a dispenser mechanism having a sliding plate disposed between a reservoir and a base plate. The sliding plate, reservoir and base plate all have corresponding holes therein, and the sliding plate is biased by a spring. When the sliding plate is moved, all of the holes between the sliding plate, reservoir and base are aligned within one another so as to allow several balls to be simultaneously discharged from the dispenser. However, it appears that the beads may "jam" the mechanism of Difiglio et al., or may even block the holes of the sliding plate such that the beads cannot be properly dispensed therefrom.

Also, U.S. Pat. No. 4,230,236 to Boulter discloses a tablet dispenser having an outer case with a front section and a rear section. The front section has integrally molded upon it an upper projecting portion and a lower projecting portion which define a gate, and an inner part. The inner part is provided with a ramp and a downward sloping groove leading to a channel. The outer case is biased by a spring. In use, the inner part is depressed and the channel is aligned with the gate such that a tablet can roll into the gate. It is noted that the tablets may block the gate during use of the Boulter tablet dispenser.

Other known systems also appear to have these same shortcomings. These systems include U.S. Pat. No. 4,405,060 to Hsei, U.S. Pat. No. 4,415,098 to Hass and U.S. Pat. No. 4,937,048 to Sakai et al., for example.

There thus remains a need for a bead dispenser which is capable of ensuring that beads do not block or otherwise bridge a ball receiving channel, which would otherwise result in a possible test failure or incorrect bead distribution. There also remains a need for a bead dispenser device that can store and dispense beads in a hermetically-sealed manner.

SUMMARY OF THE INVENTION

It is an object of the present invention to provide a bead dispenser which is capable of preventing blockage or bridging of a bead receiving channel caused by a bottleneck of several biomaterial-coated beads at the inlet of the bead receiving channel.

It is a further object of the present invention to provide a return spring mechanism which is integral with an inner bead storage chamber of the bead dispenser.

It is still another object of the present invention to provide a spring mechanism which contacts and agitates the biomaterial-coated beads within the bead holding chamber.

It is another object of the present invention to provide a bead dispenser capable of storing and serially dispensing biomaterial-coated support beads in a hermetically-sealed manner.

According to the present invention, a bead dispenser dispenses a biomaterial coated bead into a reaction tube with the biomaterial coated bead preserved in a hermetically-sealed environment up until it is dispensed into a reaction tube. The bead dispenser also ensures that the biomaterial coated beads are properly dispensed into the reaction tube without any blockage or bridging occurring at a bead receiving channel prior to the dispensing of the beads thereof.

To accomplish these objectives, the bead dispenser of the present invention has an inner bead storage chamber that stores and feeds beads directly into a base defining a plunger chamber, via a bead receiving channel. A plunger is provided within the plunger chamber that is capable of horizontal reciprocal movement within the chamber between the bead receiving channel and a bead exit opening. The plunger includes a bead holding chamber for storing and transporting the beads from the bead receiving channel to an exit opening.

In the resting position, the bead holding chamber is aligned with the bead receiving channel. In the dispensing position, the bead holding chamber of the plunger is aligned with the bead exit opening in the base of the dispenser. In this latter position, the bead housed within the bead holding chamber will "drop" from the bead holding chamber by the force of gravity.

A return spring is used to impose a normal bias on the plunger, and to agitate the beads within the inner bead storage chamber. In the resting position, the return spring biases the plunger to the resting position such that the bead holding chamber in the plunger is aligned with the bead receiving channel. However, when the plunger is displaced by an external horizontal force in opposition to and greater than the bias imposed by the return spring, the plunger can be displaced within the chamber such that the bead holding chamber aligns with the bead exit opening. A bead carried in the bead holding chamber of the plunger will then "drop" from the dispenser as the bead holding chamber aligns with the exit opening. Once the external force is removed, the return spring pushes the plunger back into the original resting position.

When the plunger is displaced, the return spring "flexes" and is displaced inward into the bead holding chamber. In this position, the return spring contacts and agitates the beads. The return spring also positions itself above the bead receiving channel, thereby moving all of the beads away from the bead receiving channel. This prevents "bottlenecks" at the entranceway of the bead receiving channel. The agitation of the beads including the moving of the beads away from the bead receiving channel also ensures that the beads will not block or bridge the bead receiving channel, and that the beads will be properly and sequentially dispensed from the bead dispenser.

The plunger itself is fitted with O-rings adequate to hermetically seal the interior of the storage unit from the ambient environment. That is, to ensure that the bead storage chamber is hermetically sealed at all times except during dispensing of beads from the plunger chamber. In general, O-rings are sealingly fitted onto portions of the plunger which form an air-tight seal with flanges on the inner wall of the plunger chamber. This forms an air and moisture seal between the interior of the inner bead storage chamber and the surrounding environment.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF A PREFERRED EMBODIMENT OF THE INVENTION

Figure 1:
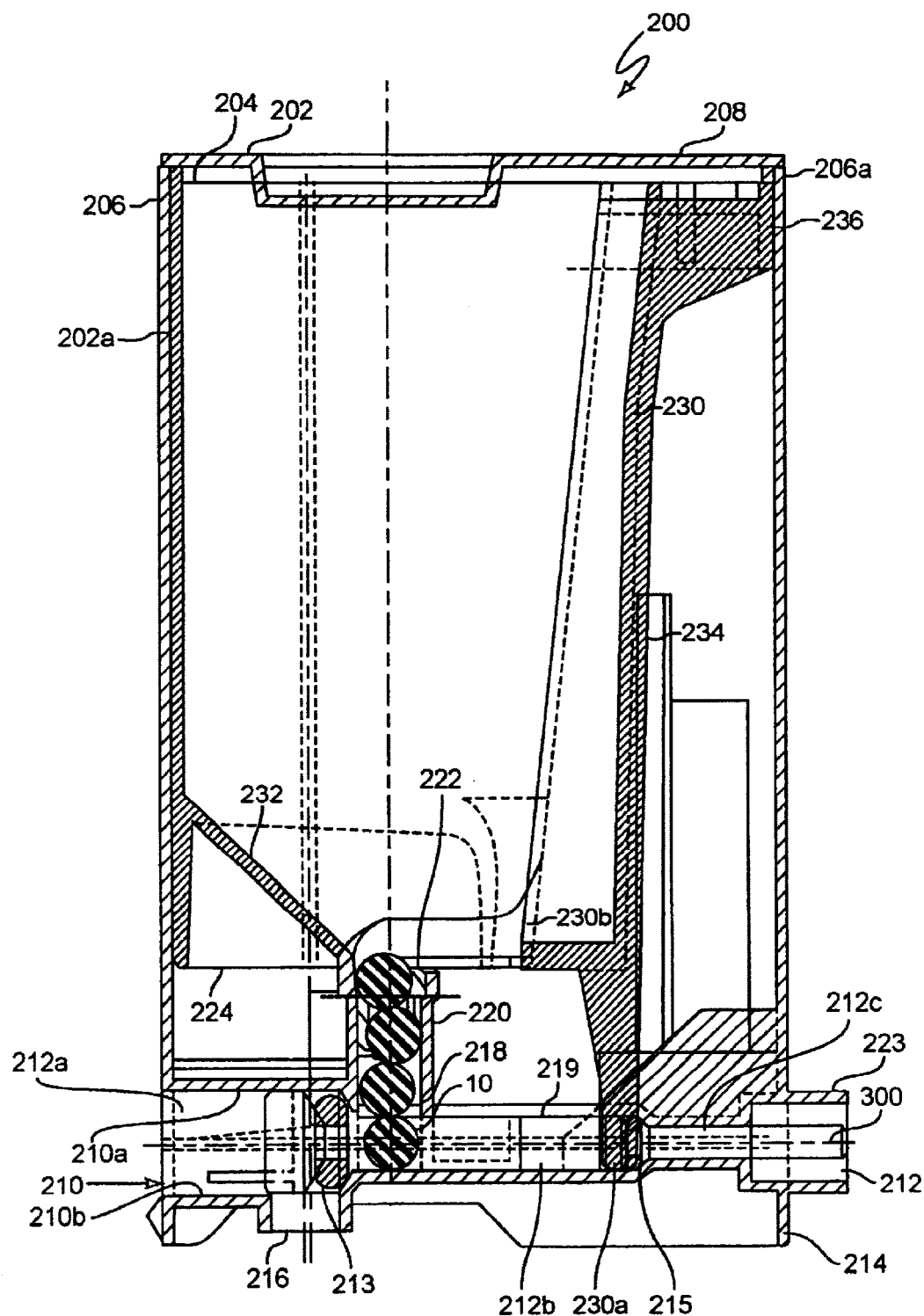
FIG. 1 is a cross-sectional side view of a bead dispenser of the present invention.

The present invention is directed to a bead dispenser and, more specifically, to a bead dispenser having a finger-like return spring which agitates the beads within the bead dispenser. The agitation of the beads within the bead dispenser prevents the beads from blocking or otherwise bridging a bead receiving channel used for apportioning the beads from an inner bead storage compartment to a bead holding chamber of a plunger mechanism for future dispensing therefrom. This ensures that all of the beads within the bead dispenser of the present invention will be properly dispensed from the bead dispenser during testing of various samples by the automated immunoassay analyzer.

In order to accomplish the objectives of the present invention, the bead dispenser includes an inner bead storage chamber having a lower downwardly sloped bottom (e.g., funnel shaped). The inner bead storage chamber holds the beads within the bead dispenser of the present invention. The funnel shaped bottom leads to a bead receiving channel, which communicates with a plunger having a bead holding chamber (in a resting position). The plunger is provided within a plunger chamber and is capable of horizontal, reciprocal movement within the plunger chamber. The plunger is biased into a first position (closed) by a return spring located within and integral to the inner bead storage chamber. Seals or O-rings are provided about the plunger in order to hermetically seal the bead dispenser when the plunger is not positioned to dispense beads therefrom.

In use, the return spring biases the plunger into the first position so that the bead holding chamber is aligned with the bead receiving channel. This allows a single bead stored within the inner bead storage chamber to be transported, via the bead receiving channel, from the inner bead storage chamber to the bead holding chamber. Once the plunger is depressed with a force greater than that imposed by the return spring, the bead holding chamber will be displaced and aligned with an exit opening at the base of the bead dispenser. This allows the bead to "drop" from the dispenser via the force of gravity. In this position, the return spring is also displaced and contacts and agitates the beads within the inner bead storage chamber in order to prevent the beads from blocking or bridging the bead receiving channel. That is, when the plunger is depressed, the return spring is biased toward an inner or second position, and contacts and agitates the beads within the inner bead storage chamber. Upon release of the plunger, the return spring returns the plunger to the first or original resting position and a subsequent bead is then provided within the bead receiving channel via the funnel shaped bottom portion of the inner bead storage chamber.

To better understand the bead dispenser of the present invention and as discussed in great detail in U.S. Pat. No. 5,773,296 (which is incorporated by reference herein in its entirety), the bead dispenser may be a subsystem of an analytical instrument intended to produce reportable assay results through the processing of specimens and various other components of the chemistry system. The beads used with the dispenser are preferably biomaterial coated beads (e.g., about 0.25 inch diameters) used as the solid phase for heterogenous immunoassays to quantitate analytes in solution. The beads are "dropped" into reaction tubes at a rate of one bead per tube, via the bead dispenser of the present invention. A plurality of bead dispensers can simultaneously reside in the system, i.e., as situated upon and traveling on a common carousel, and the operator can supplement or replace the supply of bead dispensers or packs at any time.

Referring now to the drawings, and more particularly to FIG. 1, there is shown a bead dispenser of the present invention useful for supplying, one at a time, beads for immunoassay or other chemical analysis. It is noted that the bead dispenser of the present invention is not limited in any manner whatsoever to the use in an analytical instrument, but may be used in other systems. It is noted that the bead dispenser system of the present invention is preferably used with moisture sensitive beads; however, other types of beads may equally be used with the bead dispenser of the present invention.

The bead dispenser is generally depicted as reference numeral 200 and includes an outer chamber 202 and an inner bead storage chamber 204. The outer chamber 202 is capable of accommodating two dessicant tubes within a side wall 206 and an upper cover 208. The side wall 206 and the upper cover 208 are preferably made of a rigid thermoplastic material; however, those skilled in the art should readily recognize that other materials may equally be used with the present invention. The upper cover 208 is preferably ultrasonically welded to the upper end 206a of the chamber side wall 206 after the inner bead storage chamber 204 (with beads located therein) is inserted in the outer chamber 202. The upper cover 208 hermetically seals the top end of the outer chamber 202. The hermetic seal of the cover 208 protects the beads from moisture and other contaminants.

Still referring to FIG. 1, the sidewall 206 of the outer chamber 202 may be any shape, but is preferably an oval-shape or cylindrical shell. The outer chamber 202 also includes a base 210 having an upper section 210a and a lower section 210b, which together define a plunger chamber 212. A lower extending wall 214 projects from the periphery of the lower section 210b of the bead dispenser 200, and a bead exit opening Mulhauser extends from the underside of the lower section 210b within the region defined by the lower extending wall 214.

The bead exit opening 216 has a diameter slightly larger than the bead diameters, and is offset by a predetermined distance from a bead receiving opening 218 formed in the upper section 210a of the outer chamber 202. An upward extending wall 220 extends substantially around the bead receiving opening 218 and is used to firmly hold a bead receiving channel 222 formed at a bottom portion of the inner bead storage chamber 204. The upward extending wall 220 also forms a portion of a lower portion of the bead receiving channel 222.

The plunger chamber 212 of FIG. 1 houses a plunger 300 (as described in FIG. 5) and includes three different sized diameter sections forming corresponding flanges between the sections. The first plunger chamber section 212a has a first diameter, larger than the diameters of the remaining second and third plunger chamber sections 212b, 212c. The bead exit opening 216 is preferably positioned on the underside of the first plunger chamber section 212a.

The second plunger chamber section 212b has a second diameter smaller than the diameter of the first plunger chamber section 212c but larger than the diameter of the third plunger chamber 212c. This forms a first flange 213 between the first and second plunger chamber sections and a second flange 215 between the second and third plunger chamber sections. Preferably, the first flange 213 is inclined at a relatively sharper acute angle of approximately 30° from vertical and the second flange 215 is inclined at an acute angle of approximately 60° from vertical. Those skilled in the art should recognize that the present invention is not limited by the angles of the flanges or diameter sizes of the chamber sections, and that other angles and diameters are contemplated for use by the present invention.

The second plunger chamber section 212b also includes a top section having a lateral recess 219 which communicates with an inner portion 202a of the outer chamber 202. A receiving opening 218 communicates with the bead receiving channel 220. A flange 223 extends outward from the third plunger chamber section 212c which is used to accommodate the distal end of the plunger 300 when the plunger 300 is in the original resting position (e.g., first position).

Figure 2:
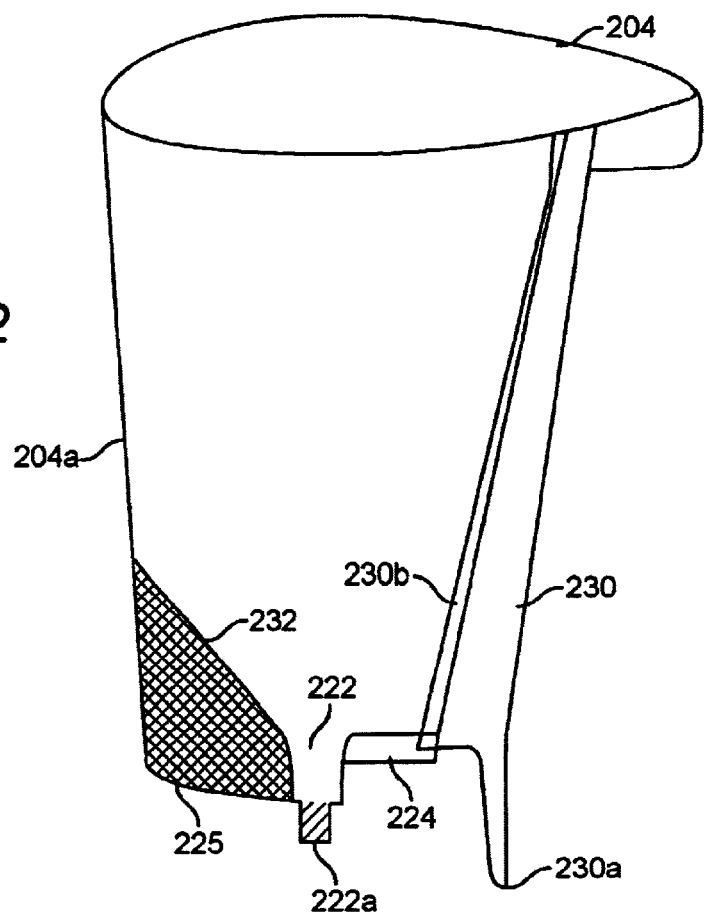
FIG. 2 is a perspective view of an inner bead storage chamber adapted for use with the bead dispenser of the present invention.

Referring now to FIGS. 1 and 2, the inner bead storage chamber 204 is mounted within the outer chamber 202, and includes sidewall 204a preferably made of a rigid thermoplastic material. The inner bead storage chamber 204 also includes a downwardly sloped bottom portion 232 (e.g., funnel shaped) which communicates with the bead receiving channel 222 formed at the base of the funnel shaped bottom portion 232. A downward extending guide wall (tab) 222a extends downward from the bead receiving channel 222 and adjoins with the upward extending wall 220 (when the inner bead storage chamber 204 is inserted within the outer chamber 202). The downward extending guide wall 222a not only ensures that the bead receiving channel 222 is properly aligned with the bead receiving opening 218 formed in the upper section 210a of the outer chamber 202, but also forms a lower portion of the bead receiving channel 222 in combination with the upward extending wall 220.

FIGS. 1 and 2 also show an integrally formed downward extending finger-like return spring 230 formed with a top portion 236 of the inner bead storage chamber 204. The return spring 230 is made of a rigid thermoplastic material or other material which is rigid but which will flex or spring back to an original position if deflected at an unfixed end. The return spring 230 extends beyond a downward extending base 225 of the inner bead storage chamber 204 so that it can communicate with the plunger 300.

The return spring 230 includes an inwardly extending portion 230b and a terminal end portion 230a. The inwardly extending portion 230b communicates with the interior portion of the inner bead storage chamber 204 and extends to approximately a centerline of the bead receiving channel 222 (in the flexed position), while the terminal end portion 230a extends within the lateral opened recess 219 of the second plunger chamber section 212b and communicates with a notch located on the plunger 300. The lateral opened recess 219 allows the return spring 230 move with the plunger 300 during the dispensing of any beads by the bead dispenser of the present invention and further allows the return spring 230 to return the plunger 300 to its original resting position.

Figure 3:
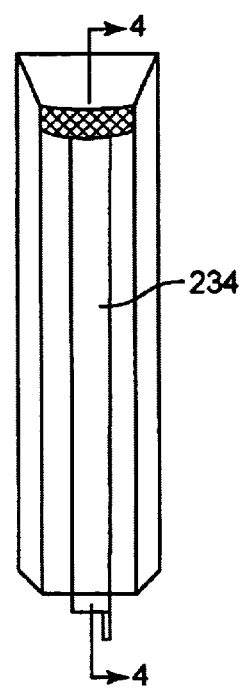
FIG. 3 is a partial front view of the inner bead storage chamber of the present invention.

FIG. 3 shows a front view of the inner bead storage chamber 204 without the return spring 230 integrally attached thereto. It should be understood by those skilled in the art that FIG. 3 is shown for illustrative purposes only and that, in use, the return spring 230 is integrally formed with the inner bead storage chamber 204. Referring now to FIG. 3, a lateral recess 234 is located at the side and bottom of the inner bead storage chamber 204. This lateral recess 234 is aligned with the return spring 230 (not shown) and allows the inwardly extending portion 230b of the return spring 230 to communicate with the interior of the inner bead storage chamber 204. This allows the inwardly extending portion 230b of the return spring 230 to agitate the beads located within the inner bead storage chamber 204, and more specifically to move the beads away from an entranceway of the bead receiving channel 222 during the dispensing process. This ensures that the beads will not become "bottle-necked" at the entranceway of the bead receiving channel 222 thus preventing any blockage or bridging at the bead receiving channel 222.

Figure 4:
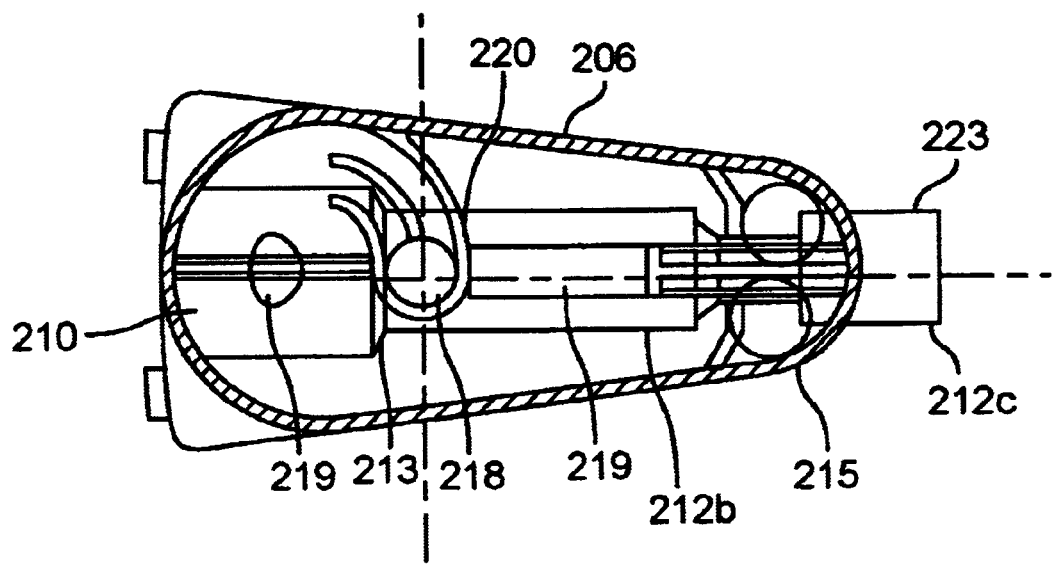
FIG. 4 is a cross-sectional view of the bead dispenser of the present invention along line 4—4 of FIG. 1.

FIG. 4 shows a cross-sectional view of the bead dispenser 200 along line 4—4 of FIG. 1. In this view, the outer chamber 202 is shown as a substantially oval shaped chamber; however, other shapes are also contemplated for use with the present invention. As further seen in FIG. 4, the plunger chamber 212 includes the first, second and third plunger chambers 212a, 212b, 212c. The bead exit opening 216 is positioned on the underside of the first plunger chamber section 212a and the lateral opened recess 219 and the bead receiving opening 218 are located on the upperside of the second plunger chamber section 212b. The upward extending wall 220 partially surrounds the bead receiving opening 218 and forms a portion of the lower part of the bead receiving channel when the inner bead storage chamber 204 is inserted within the outer chamber 202. FIG. 4 also shows the first flange 213 located between the first and second plunger chamber sections and the second flange 215 located between the second and third plunger chamber sections.

Figure 5:
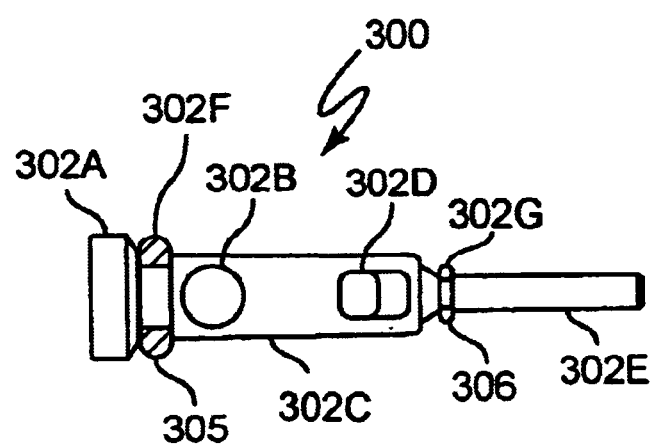
FIG. 5 is a top view of a plunger of the present invention.

FIG. 5 shows a top view of the plunger 300. Specifically, the plunger 300 may be made from any rigid material, such as hard plastic, metal, etc., but is preferably made from the same material as the inner bead storage chamber 204, itself. The plunger 300 includes a first end having a head 302a, a medial portion 302c and a distal neck 302e. The head 302a, medial portion 302c and distal neck 302e may be any shape that conforms with the shape of the plunger chamber 212. Specifically, (i) the head 302a is sized to slidably fit within the first plunger chamber section 212a, (ii) the medial section 302c is sized to slidably fit within the second plunger chamber section 212b and (iii) the distal neck 302e is sized to slidably fit within the third plunger chamber section 212c as well as the flange 223.

The plunger 300 also includes a bead holding chamber 302b that is sized to accommodate unrestricted movement of a single bead 10 (shown in phantom lines in FIG. 1) to enter, temporarily reside within, and egress the bead holding chamber 302b. This allows the bead 10 to be transported from the bead receiving channel 222 to the bead exit opening 216 for dispensing into a reaction tube.

FIG. 5 further shows a notch 302d on the plunger 300 which communicates with the terminal end portion 230a of the return spring 230. By allowing the terminal end portion 230a of the return spring 230 to communicate with the notch 302d, the plunger 300 is capable of being returned to its original closed position after the plunger has been depressed and released by a user or analytical analyzer, via the flex (biasing force) of the return spring 230.

A first collar portion 302f and a second collar portion 302g are also provided on the plunger 300 of FIG. 5. In the original resting position, the first collar portion 302f is positioned adjacent to the first flange 213 and the second collar portion 302g is positioned adjacent to the second flange 215 of the plunger chamber 212. The combination of the flanges and the collars limits the horizontal movement of the plunger 300 within the plunger chamber section 212. The collar portions 302f and 302g have O-rings (or other sealing gaskets) 305, 306, respectively, which hermetically seal the bead dispenser of the present invention when the plunger 300 is in the original resting or first position. That is, the O-rings (or other sealing gaskets) 305, 306, respectively, sealingly engage the first and second flanges 213, 215 of the plunger chamber 212 when the plunger 300 is in the closed position. This is accomplished by the preload of the return spring 230 which biases the plunger 300 into the closed position. Thus, much like the cover 208, the plunger is hermetically sealed in order to protect the beads form moisture and other contaminants. It is noted that overtravel of the plunger 300 may result due to a "soft stop" created at the O-ring 306 on the more gentle slope presented by the surface of the flange 215.

Figure 6:
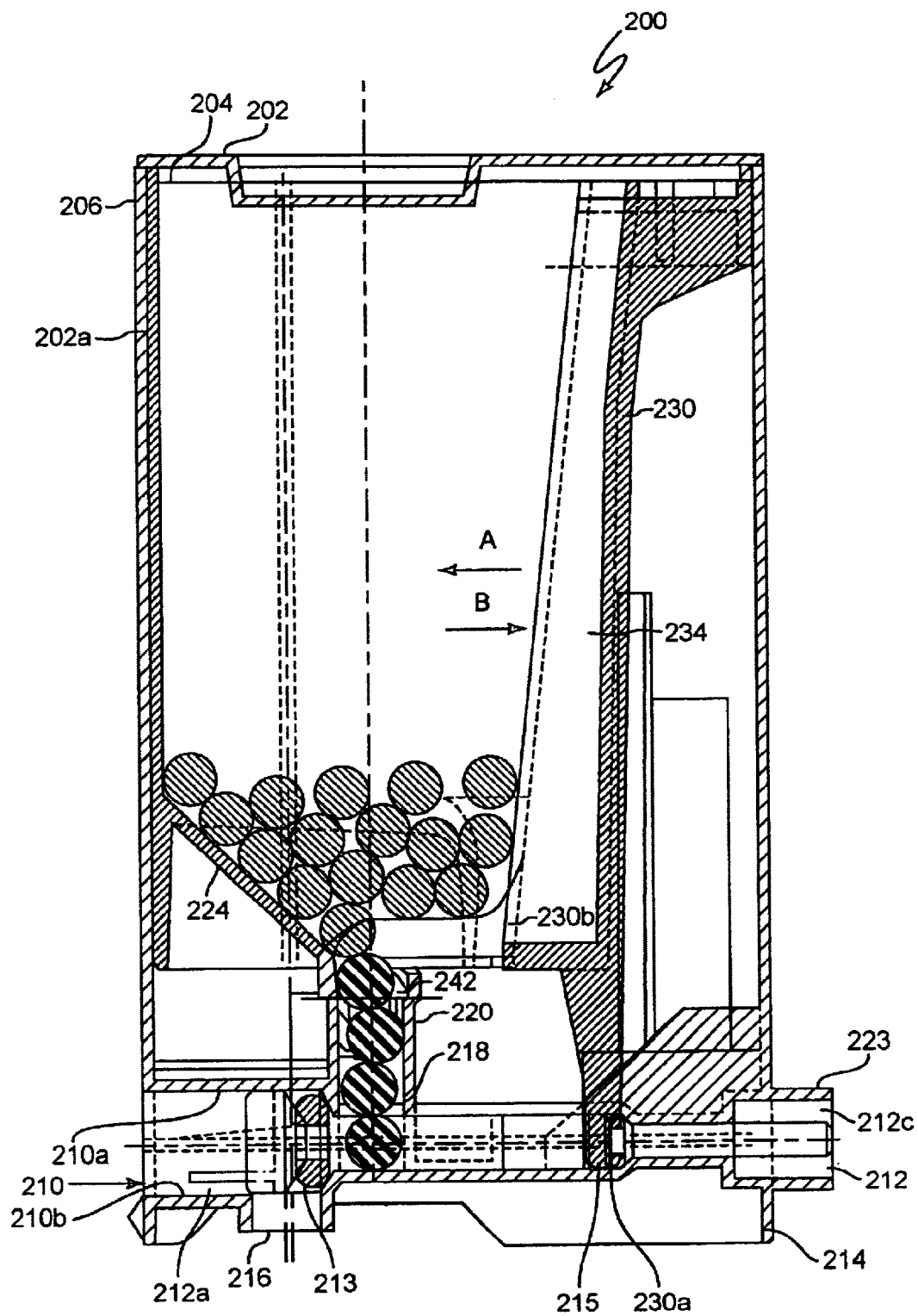
FIG. 6 is a cross-sectional side view of the bead dispenser with a return spring biasing the plunger in an original resting position.
Figure 7:
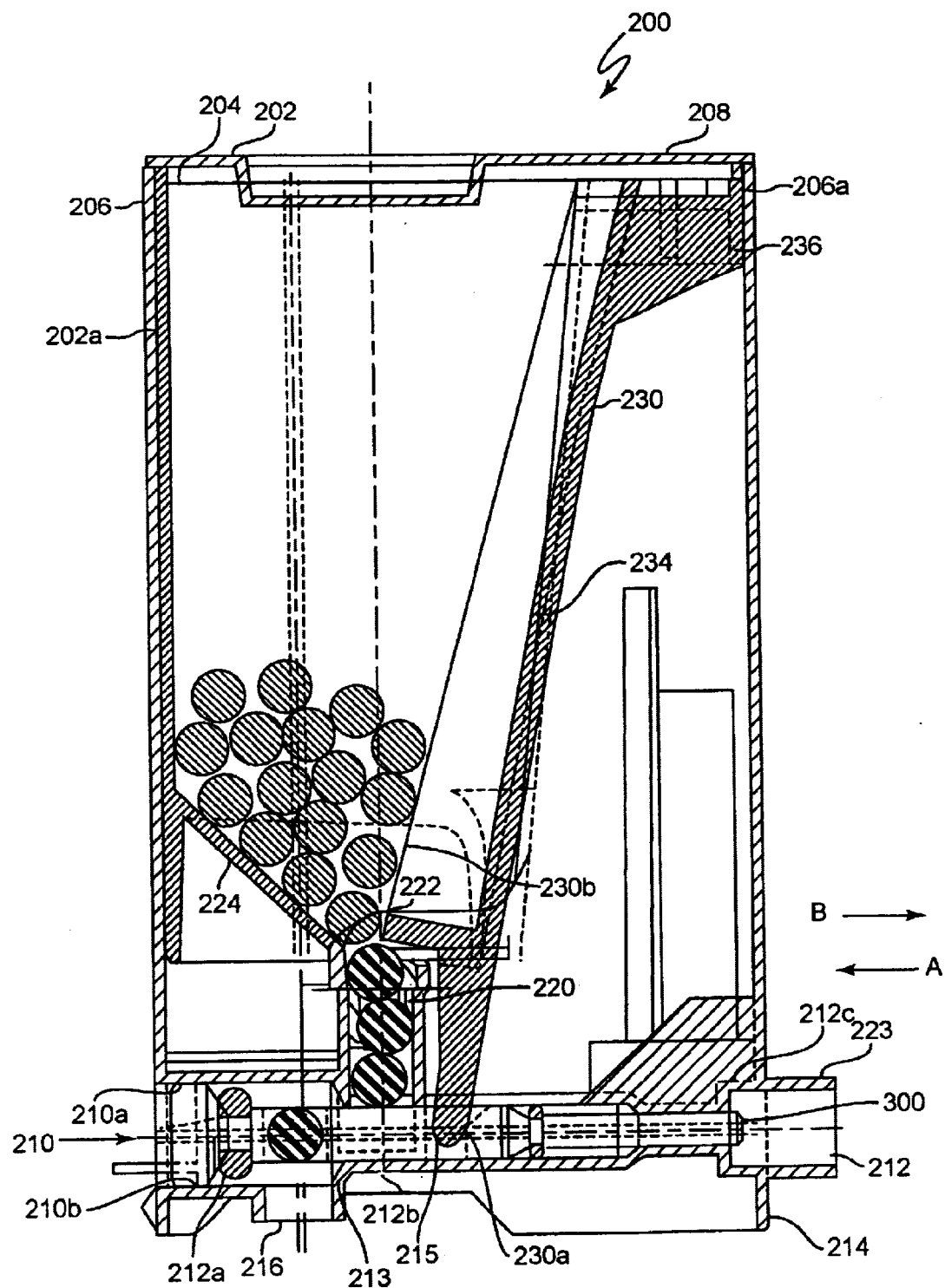
FIG. 7 is a cross-sectional side view of the bead dispenser with the plunger displaced in a second or opened position.

Referring now to FIGS. 6 and 7, in use, beads 10 are housed within the inner bead storage chamber 204. In a non-dispensing or closed position of FIG. 6, the O-ring 305 sealingly engages against the first flange 213 and the second O-ring 306 sealingly engages against the second flange 215 of the plunger chamber 212 to provide a hermetic seal. In this position, the bead dispenser 200 is hermetically sealed, and the bead receiving channel 222 is aligned with the bead holding chamber 302b (of the plunger) so that beads can be transported from the inner bead storage chamber 204 to the bead holding chamber 302b for dispensing therefrom. The plunger 300 also blocks the bead exit opening 216. The return spring 230 is in a resting or non-flexed position which provides the necessary force (i.e., internal opposing biasing force) on the plunger 300 to maintain the hermetic seal, and the terminal end 230a of the return spring 230 extends within the lateral recess 219 and into the notch 302d of the plunger 300.

As seen in FIG. 7, when the plunger 300 is provided with an actuation force (e.g., depressed or moved in the direction of arrow "A"), the bead 10 located within the bead holding chamber 302b is transported from the bead receiving channel 222 to the exit opening 216. In this manner, the bead 10 is dispensed from the bead dispenser of the present invention to a mouth of a reaction tube (or to intermediary means such as tubing used to transport the bead to a reaction tube), via the force of gravity.

As further seen in FIG. 7, when the plunger 300 is depressed or moved in the direction of arrow "A" to overcome the internal opposing biasing force of the return spring 230, the return spring 230 flexes and extends into the interior portion of the inner bead storage chamber 204. The range of movement of the return spring 230 during the dispensing operation is preferably between an initial angle of approximately 3.5° to the vertical (in the original resting position of FIG. 6) to an angle of approximately 9.5° to the vertical in the position of FIG. 7.

In the position shown in FIG. 7, the return spring 230 contacts and agitates the beads 10 within the inner bead storage chamber 204, and more specifically moves all of the beads 10 within the inner bead storage chamber 204 away from the entranceway of the bead receiving channel 222. The movement of the beads 10 is due to the inwardly extending portion 230b extending to approximately the centerline of the bead receiving channel 222. The agitation of the beads 10 which includes moving the beads away from the entranceway of the bead receiving channel 222 ensures that the bead receiving channel 222 will not become blocked or bridged during use of the bead dispenser of the present invention. As seen in both FIGS. 6 and 7, there is a vertical queue of at least three beads 10 within the bead receiving channel 222. This ensures that in the event that the return spring 230 does not dislodge the beads during a single cycle, beads can still be discharged from the bead dispenser of the present invention until further beads are dislodged.

After the bead 10 is dispensed from the bead dispenser 200, the applied force is withdrawn from the plunger and the internal biasing forces imposed by the return spring 230 automatically returns the plunger 300 to the original resting position of FIG. 6. The return of the return spring 230 to the original non-flexed position allows the next bead 10a to gently enter the bead receiving channel 222 without any blocking or bridging. At this time, the bead holding chamber 302 re-aligns with the bead receiving channel 222 so that the next bead 10b that had been waiting in the bead receiving channel 222 will drop by the force of gravity and by virtue of the weight of the column of beads there behind, into the now vacant bead holding chamber 302b of the plunger 300.

In the preferred embodiment, the O-ring 306 contacts the second flange 215 before the O-ring 305 contacts the first flange 213 when the plunger is returned to its original resting position of FIG. 6. This allows a variable degree of compression of the O-ring 306 against the surface of the second flange 215 until the O-ring 305 makes a "hard stop" with the steep surface of first flange 213. The arrangement of flanges 215, 213 with O-rings 306, 305, respectively, also prevents sliding friction from occurring between the plunger chamber 212 and the plunger 300.

The bead dispenser of this invention can serve the following functions:

a) to protect the beads contained therein from environmentally induced damage;

b) to package the beads in a fashion convenient for operator access and handling;

c) to facilitate the dispensing of a single bead into each reaction tube as needed without blockage;

d) to provide the necessary space for identification and product labeling; and e) to enable visual estimation of bead inventory by the operator.

While the invention has been described in terms of a single preferred embodiment, those skilled in the art will recognize that the invention can be practiced with modification within the spirit and scope of the appended claims.

Having thus described our invention, what we claim as new and desire to secure by Letters Patent is as follows:

1. A bead dispenser, comprising:

an outer housing having an inner portion and a plunger chamber, the plunger chamber having an upper surface and a lower surface;

a bead receiving opening located on the upper surfaces of the plunger chamber and communicating with the inner portion of the outer housing;

a bead exiting opening located on the lower surface of the plunger chamber and being offset by a predetermined distance from the bead receiving opening;

a plunger positioned within the plunger chamber, the plunger being capable of horizontal reciprocal movement within the plunger chamber between the bead receiving opening and the bead exit opening, the plunger having a bead holding chamber which is aligned with the bead receiving opening in a first position and aligned with the bead exiting opening in a second position;

an inner bead storage chamber and including an inwardly extending portion positioned within the outer housing for storing beads therein, the inner bead storage chamber having a bead receiving channel aligned with the bead receiving opening;

a return spring positioned in the inner bead storage chamber, the return spring biasing the plunger in the first position and being displaced within the inner bead storage chamber when the plunger is actuated into the second position, inwardly extending portion of the return spring contacting and agitating the beads in the inner bead storage chamber when the plunger is displaced to the second position.

2. The bead dispenser of claim 1, wherein the plunger chamber includes:

a first plunger chamber section having a first diameter;

a second plunger chamber section having a second diameter smaller than the diameter of the first plunger chamber; and a third plunger chamber section having a third diameter smaller than the diameter of the second plunger chamber section.

3. The bead dispenser of claim 2, further comprising:

a first flange located between the first and second plunger chamber sections; and a second flange located between the second and third plunger chamber sections.

4. The bead dispenser of claim 3, wherein the first flange is inclined at a first angle from vertical and the second flange is inclined at a second angle from vertical, the first angle being smaller than the second angle.

5. The bead dispenser of claim 3, wherein the plunger includes a first end having a head, a medial portion and a distal neck, each having a shape which conforms to an inner shape of the first, second and third plunger chamber sections, respectively.

6. The bead dispenser of claim 5, wherein:

the plunger includes:

a first collar portion positioned between the head and the medial portion of the plunger; and a second collar portion positioned between the medial portion and the distal neck of the plunger, wherein the first collar portion is positioned adjacent to the first flange and the second collar portion is positioned adjacent to the second flange of the plunger chamber when the plunger is in the first position.

7. The bead dispenser of claim 5, further comprising:

a first seal adjacent the first collar; and a second seal adjacent the second collar, the first seal and the second seal sealingly engage the first flange and the second flange of the plunger chamber to provide a hermetic seal when the plunger is in the first position.

8. The bead dispenser of claim 2, wherein the bead receiving opening is located on an upper surface of the second plunger chamber section and the bead exit opening is located on an underside surface of the first plunger chamber section.

9. The bead dispenser of claim 2, further comprising a lateral recess adjacent to the bead receiving opening, the lateral recess allowing a distal end of the return spring to move with the plunger from the first position to the second position.

10. The bead dispenser of claim 1, wherein the bead holding chamber of the plunger holds a single bead.

11. The bead dispenser of claim 10, wherein the bead holding chamber transports the single bead between the bead receiving channel and the bead exit opening when the plunger is displaced from the first position to the second position.

12. The bead dispenser of claim 1, wherein the plunger includes a notch which communicates with a terminal end portion of the return spring.

13. The bead dispenser of claim 1, wherein the outer housing includes an upper cover ultrasonically welded to an upper end of the outer housing when the inner bead storage chamber is placed within the outer housing, the upper cover hermetically seals the outer housing.

14. The bead dispenser of claim 1, further comprising a lower extending wall projecting around a periphery of the outer housing, the lower extending wall projecting downward lower than the bead exit opening.

15. The bead dispensing of claim 1, further comprising an upward extending wall extending substantially around the bead receiving opening within the inner portion of the outer housing.

16. The bead dispenser of claim 15, further comprising a tab extending downward from the bead receiving channel, the tab and the upward extending wall combine to form a lower portion of the bead receiving channel.

17. The bead dispenser of claim 16, wherein the upward extending wall and the tab align the bead receiving channel with the bead receiving opening.

18. The bead dispenser of claim 16, wherein the upward extending wall in combination with the downward tab firmly hold the bead receiving channel in alignment with the bead receiving opening.

19. The bead dispenser of claim 1, wherein the inner bead storage chamber includes a downwardly sloped bottom portion having a base, the bead receiving channel is formed at the base of the funnel shaped bottom portion.

20. The bead dispenser of claim 1, wherein the inner bead storage chamber includes a lateral recess aligned with the return spring, the lateral recess permitting the return spring to move inwardly to the inner portion of the inner bead storage chamber when the plunger is actuated into the second position, thereby contacting and agitating the beads in the inner bead storage chamber.

21. The bead dispenser of claim 20, wherein the return spring includes an inwardly extending portion, the inwardly extending portion being positioned at an approximate centerline of the bead receiving channel when the plunger is displaced into the second position.

22. The bead dispenser of claim 21, wherein the inwardly extending portion of the return spring partially blocks the bead receiving channel when the plunger is displaced into the second position.

23. The bead dispenser of claim 21, wherein:

a first bead drops into the bead holding chamber of the plunger when the return spring returns the plunger into the first position and aligns the holding chamber with the bead channel opening; and a second bead of the beads within the inner bead storage chamber drops into the bead receiving channel when the return spring returns the plunger into the first position.

24. The bead dispenser of claim 1, wherein when the plunger is in the first position, the plunger blocks the bead exit opening and the inner bead storage chamber is hermetically sealed via sealing members located on the plunger which engage surfaces within the plunger chamber.

* * * * *